United States Patent [19]

Löbermann et al.

[11] Patent Number: 5,097,019

[45] Date of Patent: Mar. 17, 1992

[54] PHARMACEUTICAL CONTAINING TISSUE PROTEIN PP4, A PROCESS FOR THE PREPARATION OF PP4 AND FOR THE PASTEURIZATION THEREOF, AND THE USE OF PP4

[75] Inventors: Hartmut Löbermann, Weimar; Christiane Bornmann, Gemünden, both of Fed. Rep. of Germany

[73] Assignee: Behringwerke Aktiengesellschaft, Marburg/Lahn, Fed. Rep. of Germany

[21] Appl. No.: 649,552

[22] Filed: Feb. 1, 1991

Related U.S. Application Data

[62] Division of Ser. No. 354,204, May 19, 1989, abandoned, which is a division of Ser. No. 133,621, Dec. 16, 1987, abandoned.

[30] Foreign Application Priority Data

Dec. 18, 1986 [DE] Fed. Rep. of Germany ....... 3643182

[51] Int. Cl.$^5$ .......................... C07K 3/18; C07K 3/20; C07K 3/22
[52] U.S. Cl. .................................... 530/392; 530/395; 530/412; 530/415; 530/416; 530/417
[58] Field of Search ...................... 514/8, 21; 530/392, 530/395; 500/412, 415, 416, 417

[56] References Cited

U.S. PATENT DOCUMENTS

| 4,507,229 | 3/1985 | Bohn | 530/392 |
| 4,562,072 | 12/1985 | Heimburger et al. | 514/21 X |
| 4,990,597 | 2/1991 | Löbermann | 530/392 |

FOREIGN PATENT DOCUMENTS 0123307 10/1984 European Pat. Off.
0217341 4/1987 European Pat. Off.

OTHER PUBLICATIONS

Reutelingsperger et al., European Journal of Biochemistry 151: 625–629 (1985).

Primary Examiner—Howard E. Schain
Attorney, Agent, or Firm—Finnegan, Henderson, Farabow, Garrett and Dunner

[57] ABSTRACT

An agent for the therapy or prophylaxis of disturbances of hemostasis, which contains tissue protein PP4, a process for the purification of PP4 by means of a hydrophobic adsorbent which is insoluble in water, and a process for the pasteurization of a solution containing PP4 in the presence of calcium ions and of at least one mono- or oligosaccharide or sugar alcohol and, where appropriate, of an amino acid, and the use of PP4, are described.

2 Claims, No Drawings

PHARMACEUTICAL CONTAINING TISSUE PROTEIN PP4, A PROCESS FOR THE PREPARATION OF PP4 AND FOR THE PASTEURIZATION THEREOF, AND THE USE OF PP4

This is a division of application Ser. No. 07/354,204 filed May 19, 1989 which was a division of application Ser. No. 07/133,621, filed Dec. 16, 1987, both now abandoned.

The invention relates to an agent containing tissue protein PP4 for inhibiting blood clotting, to a process for the preparation of PP4 and a process for the pasteurization thereof, and to the use of PP4.

The glycoprotein PP4, which is found, for example, in placenta, is described in DE 33 15 000 A 1 (U.S. Pat. No. 4,507,229). PP4 has a molecular weight of 35,000±5,000 Dalton and an isoelectric range of pH 4.85±0.15.

Anticoagulant proteins can be divided into several groups on the basis of their mode of action. Both the group of proteinase inhibitors such as, for example, antithrobin III, and that of the proteinases, for example activated protein C, are associated with some disadvantageous properties for anticoagulant therapy, because they either do not act until the activated clotting enzyme stage or inactivate clotting factors by proteolysis thereof, "consuming" them.

Hence the object of the invention was to make available an agent which inhibits blood clotting and is able to prevent blood clotting without resulting in consumption of clotting factors.

DE 35 33 516 A 1, (pages 6 to 8) describes anticoagulant proteins which are reported to have an isoelectric range of 4.4–4.6. These proteins are isolated from the intima of major vessels, for example the aorta or umbilical cord.

Moreover, the properties of PP4 are described as follows in DE 33 15 000 A1 (U.S. Pat. No. 4,507,229): an electrophoretic mobility in the range between that of $alpha_1$ and $alpha_2$ globulins; a sedimentation coefficient $s_{20,w}$ of 3.3±0.2 S; an extinction coefficient $E_1^{1\%}{}_{cm}$ (280 nm) of 5.9±0.5; a carbohydrate content of 2.4±0.94% (g/100 g) (mannose 0.3±0.2%, galactose 0.4±0.2%, xylose 0.1±0.04%, glucose 0.2±0.1%, glucosamine 1.0+2%, neuraminic acid 0.4±0.2%) and the following amino acid composition:

| Amino acid | Residues per 100 residues (mol %) | Coefficient of variation |
|---|---|---|
| Lysine | 6.95 | 1.14 |
| Histidine | 0.97 | 17.4 |
| Arginine | 5.44 | 1.77 |
| Aspartic acid | 11.41 | 1.68 |
| Threonine | 6.78 | 2.40 |
| Serine | 6.21 | 2.26 |
| Glutamic acid | 12.25 | 0.43 |
| Proline | 1.96 | 6.20 |
| Glycine | 6.68 | 3.83 |
| Alanine | 7.92 | 1.67 |
| Cystine ½ | 0.77 | 19.5 |
| Valine | 5.34 | 3.80 |
| Methionine | 1.98 | 6.00 |
| Isoleucine | 5.21 | 2.23 |
| Leucine | 11.50 | 0.45 |
| Tyrosine | 3.55 | 4.21 |
| Phenylalanine | 4.07 | 3.77 |
| Tryptophan | 0.93 | 23.9 |

It has been found, surprisingly, that this glycoprotein PP4 has anticoagulant properties. Thus the invention relates to the use of the glycoprotein PP4 for inhibiting blood clotting.

The invention also relates to an agent of the therapy or prophylaxis of disturbances of hemostatis, which contains an effective amount of PP4 and a pharmaceutically suitable vehicle and/or stabilizer.

In a solution, an agent of this type preferably contains 0.001–100 mg of PP4 per ml of solution. It is administered in a dose of, for example, 0.001–50 mg per kg of body weight once or several times a day as a bolus or as a continuous drip.

A PP4-containing agent of this type is preferably prepared either in the form of a lyophilisate, where appropriate with stabilizers and additives such as, for example, albumin, gelatin, salts, sugars and/or amino acids, or in the form of an aqueous solution which is isotonic with blood and contains, where appropriate a bactericide and stabilizers such as, for example, albumin, gelatin, salts, sugars and/or amino acids. The solution can be administered, for example, by parenteral injection or perfusion.

It is also possible to use in the sense according to the invention a PP4 which has been prepared by gene manipulation.

Relatively large amounts of PP4 are needed for use as pharmaceutical. This is why a straightforward process for isolation from tissues is desirable.

It has been found, surprisingly, that PP4 from a tissue extract or a solution can be bound to a hydrophobic carrier matrix and then, by stepped or gradient elution, can have impurities very extensively removed.

Hence the invention relates to a process for the purification of PP4, which comprises contacting a solution containing PP4, preferably a tissue extract containing PP4, with a hydrophobic adsorbent which is insoluble in water, removing the adsorbent from the supernatant solution, where appropriate washing with a buffer, and eluting the PP4.

It is also possible, before or after this process, to carry out, where appropriate, other known purification processes such as ion exchange chromatography, gel filtration or adsorption onto calcium phosphate or hydroxyapatite.

In a preferred procedure for purifying PP4, the solution containing PP4 is, at a pH of 5.5–9.5, a temperature of 0° C. to 40° C. and after addition of salts, for example after addition of 50–250 g of ammonium sulfate/l of solution, magnesium sulfate or 0.5–3 mol/l NaCl, LiCl or KCl, contacted with a hydrophobic adsorbent which is insoluble in water, for example a carrier material which has aliphatic, aromatic or araliphatic groups. Examples of carrier materials which can be used are $^R$Sepharose, agarose or $^R$Fractogel. The aliphatic groups which are preferably used are alkyl groups having 1 to 10 carbon atoms, for example the butyl or octyl radical, as well as, for example, optionally substituted phenyl or phenylalanyl radicals or benzyl or substituted benzyl radicals. The adsorbent is then removed from the solution, where appropriate washed with a solution which contains, for example, 50–250 g/l ammonium sulfate or 0.5–3 mol/l NaCl, LiCl or KCl, and the PP4 is eluted using a liquid of relatively low ionic strength, where appropriate by means of a gradient.

In a particularly preferred embodiment, the solution containing PP4 is, at a pH of 6–8 and after addition of a solution containing 144–243 g of ammonium sulfate/l, contacted with, for example phenyl- or phenylalanyl-$^R$Sepharose or agarose, but is very particularly preferably contacted at pH 6.5–7.8, and after addition of a solution containing 170–200 g of ammonium sulfate/l, with phenyl-$^R$Sepharose. The adsorbent is then removed from the solution, washed with, for example, a solution which contains 176–196 g of ammonium sulfate/l of solution, and the PP4 is eluted by means of a solution which contains 114–144 g of ammonium sulfate/l of solution.

It is furthermore expedient, because of the risk of transmission of diseases (hepatitis, AIDS), for biological therapeutics which are intended for use in humans to be heated to kill infectious organisms. However, this usually means loss of activity of the biological active substances.

It has been found, surprisingly, that an aqueous solution of PP4 can be heated in the presence of calcium ions and of at least one mono- or oligosaccharide or sugar alcohol and, where appropriate, an amino acid, there being very extensive retention of the anticoagulant property.

Hence the invention also relates to a process for the pasteurization of a solution containing PP4, which comprises heating this solution in the presence of calcium ions and of at least one mono- or oligosaccharide or sugar alcohol and, where appropriate, an amino acid under conditions such that pathogenic organisms are killed.

In a preferred procedure for the pasteurization of a solution containing PP4, the pH of the solution is adjusted to 5.0–9.5, and 30–150 g/100 ml of solution of at least one mono- or oligosaccharide or sugar alcohol and 0.005–2 mol/l calcium ions and, where appropriate, 0.1–1.5 mol/l of an amino acid are added. The calcium ions can be introduced in the form of, for example, calcium salts, for example as $CaCl_2$ or calcium acetate.

In a very particularly preferred embodiment, 100–150 g of sucrose/100 ml of solution and 30–100 mmol/l $CaCl_2$ are added to a solution which contains PP4 and has a pH of 6.5–8.5. After the ingredients have dissolved it is possible to heat the solution, for example, at 40°–80° C. for 1 to 20 hours, but preferably at 55°–65° C. for 8–15 hours. The content of PP4 should not be below 20 µg/ml of solution. After the heating, it is possible to process the solution further, for example by concentration, dialysis, sterile filtration and/or lyophilization.

A product obtained by the preparation and pasteurization processes described above is particularly distinguished by the very extensive removal of impurities from PP4, and its anticoagulant action being very extensively present.

A PP4 pharmaceutical can be manufactured in the customary manner using a physiologically acceptable and pharmaceutically suitable vehicle in solid or liquid form and, where appropriate, further additives such as stabilizers and auxiliaries.

Thus the invention also relates to a process for the preparation of a PP4-containing pharmaceutical for the therapy and/or prophylaxis of disturbances of hemostasis, which comprises preparation of a PP4-containing solution, to which, where appropriate, additives and stabilizers, such as, for example, albumin, gelatin, salts, sugars and/or amino acids are added, and converting this solution to a dry form, where appropriate a lyophilisate.

The examples which follow are intended to illustrate the invention.

EXAMPLE 1

Isolation of PP4 from placental tissue, and the pasteurization thereof 2 kg of deep-frozen placenta were homogenized in a tissue mincer. The homogenizate was washed 3 times with 1 liter of physiological NaCl solution each time. The placental tissue was removed from the supernatant solution by centrifugation. The washed placental homogenizate was suspended in 3 liters of $^R$Triton×100-containing buffer A (20 mmol/l tris.HCl, 50 mmol/l NaCl, 2 g/100 ml $^R$Triton×100, pH 7.4) and the suspension was stirred overnight. The extract was removed by centrifugation, and the tissue was extracted once more with 2 liters of buffer A overnight. The two extracts were combined (4.8 liters) and diluted with buffer B (20 mmol/l tris. HCl, 50 mmol/l NaCl, pH 7.5) to 15 l. 0.75 g of DEAE-$^R$Sepahadex A 50/l of solution was added, and the suspension was then stirred for 1 hour, and the adsorbate was removed from the solution, washed with 40 liters of buffer B and then with 600 ml of buffer B which contained 100 mmol/l NaCl, and PP4 was eluted with buffer B which contained 500 mml/l NaCl. 176 g/l ammonium sulfate were added to the eluate (600 ml), and the mixture was treated with 300 ml of phenyl-$^R$Sepharose either in a batch process or on a column.

The phenyl-$^R$Sepharose was equilibrated in buffer B which contained 3/10 of the saturation concentration of ammonium sulfate. After washing with the same buffer, PP4 was eluted with buffer B which contained 1/5 of the saturation concentration of ammonium sulfate. The PP4 was precipitated by increasing the ammonium sulfate concentration to 85 g/100 ml or was concentrated by means of ultrafiltration and further purified by gel filtration on ACA 54. The ACA 54 column (3×100 cm) was equilibrated in buffer B which contained 500 mmol/l NaCl. The fractions containing PP4 were combined.

Where necessary, this can be followed by a pasteurization as described in Example 3. However, the heating can also be carried out at another stage, such as the DEAE-$^R$Sepharose A50 eluate or the eluate from the phenyl-$^R$Sepharose treatment.

EXAMPLE 2

Determination of the anticoagulant activity of PP4

Modified prothrombin time (PT) and modified partial thromboplastin time (PTT) determinations were used to determine the anticoagulant activity of PP4 prepared as in Example 1.

a) Modified PT determination

150 µl of buffer A (20 mmol/l tris.HCl, 142 mmol/l NaCl, pH 7.5), 25 µl of sample or buffer B (20 mmol/l tris.HCl, 500 mmol/l NaCl, pH 7.5) and 25 µl of thromboplastin solution were added to 50 µl of standard human plasma. After incubation at 37° C. for three minutes, clotting was started by addition of 250 µl of a solution C containing $CaCl_2$ (10 mmol/l tris.HCl, 80 mmol/l NaCl, 20 mmol/l $CaCl_2$, pH 7.9) and the clotting time was determined in a Schnitger-Gross coagulometer. The clotting time of the control containing buffer B was 60 sec.

Dependence of the clotting time in the modified PT determination on the content of PP4 in the solution

| PP4 concentration (μg/ml) | 0 | 5 | 10 | 15 | 20 |
|---|---|---|---|---|---|
| modified PT (sec) | 60 | 68 | 89 | 111 | 132.5 | b) Modified PTT determination

25 μl of sample and 75 μl of buffer A which contained 100 mmol/l NaCl were added to 100 μl of standard human plasma, the mixture was incubated at 37° C. for 3 min, 50 μl of $^R$Pathromtin reagent solution were added, incubation was continued at 37° C. for 6 min, and then 50 μl of kaolin suspension were mixed in and, after a further 2 min at 37° C., the clotting was started by addition of 100 μl of $CaCl_2$-solution C.

The sample had previously been dialyzed against buffer A which contained 500 mmol/l NaCl. The contents of one container of $^R$Pathromtin reagent solution were dissolved in 1 ml of 9 g/l NaCl solution. The clotting time was determined in a Schnitger-Gross coagulometer The clotting time of the control containing buffer A was 70 sec.

Dependence of the clotting time in the modified PTT determination on the content of PP4 in the solution

| PP4 concentration (μg/ml) | 0 | 13 | 17.7 | 26 |
|---|---|---|---|---|
| modified PTT (sec) | 70 | 84 | 98 | 129 |

EXAMPLE 3

Pasteurization of a solution containing PP4

500 ml of a solution containing PP4 (100 μg of PP4/ml) were dialyzed against 20 mmol/l tris.HCl, 150 mmol/l NaCl, pH 7.5. The 100 g of sucrose 100 ml of solution were weighed in. Once the sucrose had completely dissolved, 50 mmol/l $CaCl_2$ were added. The solution can, after the heating (60° C./10 h), be dialyzed against 20 mmol/l tri—Na citrate, 60 mmol/l NaCl, 10 g/l glycine, pH 7.0, and sterilized by filtration and lyophilized.

Pasteurization of PP4 (100 μg/ml) in solution—effect of calcium ions on the stability of PP4

| | Modified PT (sec) | |
|---|---|---|
| before heating | heating without calcium | heating with 50 mmol/l calcium |
| 68 | 60 | 68 |

We claim:

1. A process for the pasteurization of a solution containing PP4, which comprises heating this solution in the presence of calcium ions and of at least one mono- or oligosaccharide or sugar alcohol under conditions such that pathogenic organisms are killed.

2. A process as claimed in claim 1, wherein the solution additionally contains an amino acid.

* * * * *